(12) United States Patent
Maillot

(10) Patent No.: US 8,469,257 B2
(45) Date of Patent: Jun. 25, 2013

(54) BOX FOR STERILE PRODUCTS

(75) Inventor: Guillaume Maillot, Colmar (FR)

(73) Assignee: DS Smith Kaysersberg, Kunheim (FR)

( * ) Notice: Subject to any disclaimer, the term of this patent is extended or adjusted under 35 U.S.C. 154(b) by 1019 days.

(21) Appl. No.: 11/885,175

(22) PCT Filed: Mar. 10, 2006

(86) PCT No.: PCT/FR2006/000537
§ 371 (c)(1),
(2), (4) Date: Jul. 9, 2010

(87) PCT Pub. No.: WO2006/095097
PCT Pub. Date: Sep. 14, 2006

(65) Prior Publication Data
US 2010/0264049 A1 Oct. 21, 2010

(30) Foreign Application Priority Data

Mar. 10, 2005 (FR) ..................................... 05 50635

(51) Int. Cl.
*B65D 5/42* (2006.01)
(52) U.S. Cl.
USPC ............. 229/120; 53/432; 53/510; 206/213.1
(58) Field of Classification Search
USPC ........ 229/120; 422/295, 297, 300; 206/213.1, 206/438, 439, 484.1; 53/111 R, 425, 428, 53/432, 510
See application file for complete search history.

(56) References Cited

U.S. PATENT DOCUMENTS

| | | | | |
|---|---|---|---|---|
| 2,506,769 A * | 5/1950 | Bergstein | .......................... | 53/432 |
| 2,533,773 A * | 12/1950 | De La Foret | .................. | 229/120 |
| 3,521,806 A * | 7/1970 | Esty | ........................... | 206/213.1 |
| 3,973,721 A * | 8/1976 | Nakane | ......................... | 229/120 |
| 4,515,266 A * | 5/1985 | Myers | ............................ | 229/120 |
| 4,550,546 A | 11/1985 | Raley et al. | | |
| 4,603,538 A | 8/1986 | Shave | | |
| 5,518,115 A | 5/1996 | Latulippe | | |
| 6,126,067 A * | 10/2000 | Grigsby et al. | ............... | 229/120 |
| 6,578,758 B1 * | 6/2003 | Grigsby et al. | ............... | 229/120 |
| 6,808,106 B1 * | 10/2004 | Grigsby et al. | ............... | 229/120 |
| 2008/0172940 A1* | 7/2008 | Huang et al. | .................. | 206/423 |

FOREIGN PATENT DOCUMENTS

JP          3187837 A   *   8/1991

* cited by examiner

*Primary Examiner* — Gary Elkins
(74) *Attorney, Agent, or Firm* — Novak Druce Connolly Bove + Quigg LLP

(57) ABSTRACT

This invention relates to a box for sterile products made of panels forming a belt (10) and of flaps extending the panels and forming bottom and top walls perpendicular to the belt, the belt and the flaps being cut in a foamed plastic material plate comprising at least two covering sheets (P1, P2) maintained mutually spaced apart by a plurality of struts (E) providing longitudinal mutually parallel cells. This invention is characterized in that at least one of the covering sheets is perforated (C) for allowing for a sterilizing gas to pass through the cover, and cuts (13) crossing at least one covering sheet of the plate are provided along hinging lines of the flaps on the belt for providing the communication of said cells with the outside when flaps (31, 32, 41, 42, 51, 52, 61, 62) are folded at right angle.

4 Claims, 1 Drawing Sheet

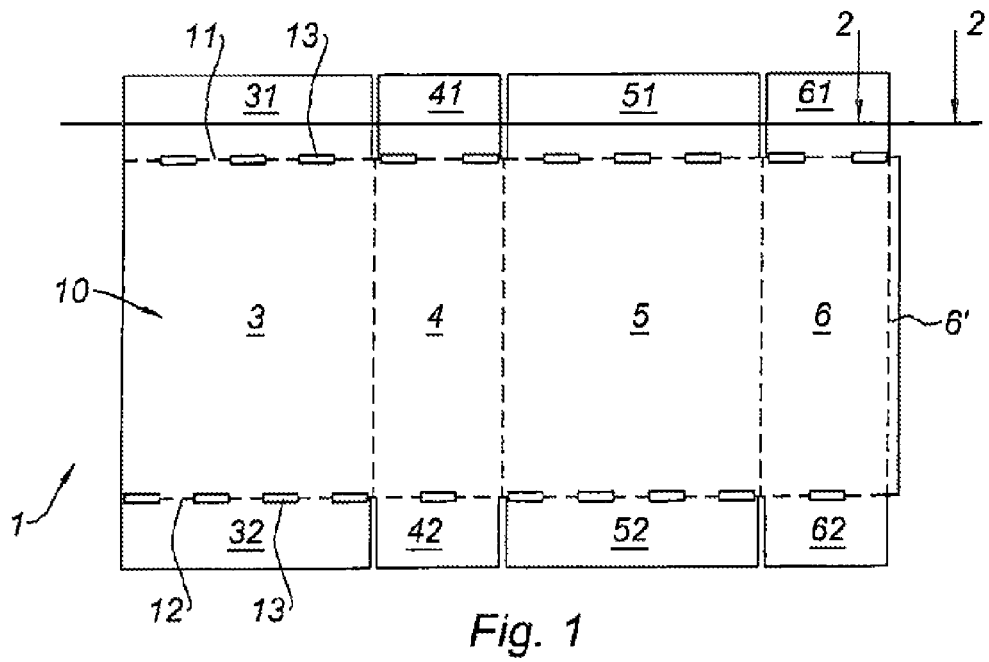
Fig. 1
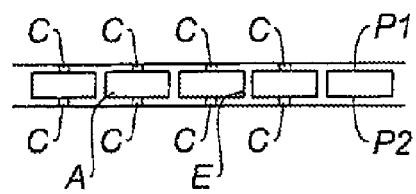
Fig. 2 - PRIOR ART
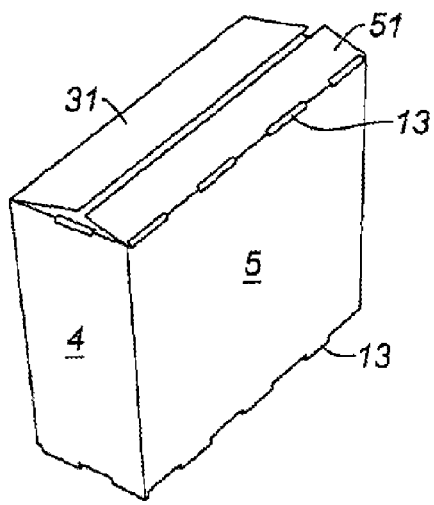
Fig. 3

BOX FOR STERILE PRODUCTS

FIELD OF THE INVENTION

The present invention relates to a box made by folding and erecting into volume a plate made in a semi-rigid plastic material for accommodating sterile products.

BACKGROUND

For packaging and shipping sterile products, such as medical or surgical instruments or items, as for example syringe containing boxes or bags, boxes made of a foamed plastic material are used, being treated together in a sterilizing enclosure with the products being contained therein. A method consists in filling the box with the involved product being as-made and not yet sterile, and then subjecting the whole set to a sterilizing treatment with an appropriate gas, such as EtO (ethylene oxide) in a sealed enclosure. After a given exposure time, up to 75 hours, the gas is vented from the enclosure and substituted with air before the product is extracted from the enclosure. The treated product is thus shipped in its box without any further handling before it reaches its destination.

The gas used for the sterilizing treatment being by nature very toxic as it is to kill any germ, it should be ensured that gas traces do not remain trapped inside the packaging. The implemented treatment procedures are provided so as to give a total safety for the operators and agents in charge of handling the boxes, including when leaving the treatment enclosure.

Foamed plastic material plates are commonly used for manufacturing packaging boxes. Such a material is both light and strong. It could be compared to corrugated cardboard, and has the additional advantage of being durable and more resistant to contamination that the latter.

The expression "foamed plastic material plates" as used herein means plates made of at least two parallel planar sheets maintained spaced apart one from the other by mutually parallel walls. Sheets and walls provide therebetween longitudinal channels referred to as cells in the art. Such plates are obtained through extruding a plastic material being selected depending on the application, such as a polyolefin, through a rectilinear die. Immediately downstream from the extrusion head, the material, still in a plastic condition, passes through sizing plates to fix the plate shape.

Such a plate type is presently widely used and is likely to replace corrugated cardboard for some applications as the one disclosed hereinabove. The standard box is the American box. It comprises a belt with four panels extended on both sides by flaps being folded at right angle for forming the bottom and the top or lid of the box.

In the case of a box to be used for sterilizing treatments, the covering sheets making up the foamed plate are perforated with a multiplicity of holes for providing a gas circulation through the latter during the treatment phase in the enclosure and preventing the latter from building up and forming residual pockets at the end of the treatment upon the gas removing step.

The Applicant has established as a goal to improve the gas circulation through the box when flaps are folded at right angles and the box is closed ready to be directly shipped after being treated in the gas sterilizing enclosure.

SUMMARY

The box according to this invention for sterile products is made of adjacent panels forming a belt and of flaps extending the panels and forming the bottom and top walls being perpendicular to the belt, the belt and the flaps being cut out in a foamed plastic material plate comprising at least two covering sheets maintained spaced apart from one another by means of a plurality of struts providing mutually parallel longitudinal cells, and is characterized in that at least one of the covering sheets is perforated so as to allow for a sterilizing gas to pass through said covering sheet, the perforations allowing for gas to pass although preventing dust from passing through, and wide cuts go across at least the other covering sheet of the plate so as to provide for the communication of said cells towards outside.

Such a solution provides for a great safety regarding the gas circulation and especially regarding the removal thereof after the treatment. Indeed, the cells form chimneys directly opening into the outside through such cuts. Such cuts are sufficiently wide for overlapping at least the width of one cell. Preferably, the perforations are provided on the plate sheet inside the box and the cuts on the external sheet.

According to a preferred feature, the cuts are provided along the flap-hinging lines on the belt.

BRIEF DESCRIPTION OF THE DRAWINGS

Hereinafter there will be described in further detail an embodiment of this invention, referring to accompanying drawings on which:

FIG. 1 illustrates a foamed plastic material plate;

FIG. 2 illustrates the structure of the plate in a sectional view along the direction 2-2 on FIG. 1; and FIG. 3 shows a box formed through erection into volume of the plate in FIG. 1, the flaps being folded.

DETAILED DESCRIPTION

As can be seen on FIG. 1, a plate 1 is traditionally cut so as to define four adjacent panels 3, 4, 5 and 6, of the belt 10. The panel 6 comprises a side section. Each of the panels is extended on each side by a flap 31 and 32, 41 and 42, 51 and 52, 61 and 62 respectively. A hinging line 11 and 12 defines the separation between the belt and the flaps. The hinge is formed through crushing the plate along such a line. Instead of one single plate folded on itself, the belt could be formed from two halves assembled along two welds.

FIG. 2 shows the plate 1 in an enlarged sectional view according to direction 2 of FIG. 1. There can be seen two covering walls P1 and P2 maintained mutually spaced apart by means of struts E being spaced one from the other and mutually parallel. Struts and covering sheets define mutually parallel channels or cells A. The cell direction is perpendicular to hinging lines 11 and 12. It could form another angle than a right one but it is not parallel to the latter.

In the prior art solution, in order to allow for gas to circulate through the plate, calibrated holes C are provided in the plate. Their diameter is sufficient for making the plate gas- or vapour-permeable. However, their diameter is small enough to prevent dirt from going through as well.

Providing such holes is not simple, as it should be insured that all the cells are permeable so as to precisely preventing any risk of toxic gas building up. In an industrial process, such a constraint results in costs, that people have tried to avoid.

According to the invention, the problem has been solved of putting into communication each of the cells with the outside through providing cuts transversal to the cell direction along the folding lines 11 and 12. Such cuts 13 are made by means of a knife through at least one of the covering sheets, the external covering sheet in such a case, or through both covering sheets. The length of each cut and the number of cuts along the plate are determined experimentally. Such cuts could be simple grooves made with a blade through one or both covering sheets. They could also be so formed that the cut edges are mutually spaced apart. Spacing could be of a few millimetres.

There is shown on FIG. 3 the box formed after folding and erection into volume of the plate in FIG. 1. Through folding flaps, the cut edges 13 are cleared and the cells form chimneys opening into the open air. It could be observed that cuts are provided so that preferably all the cells are in communication with the box outside. Advantageously, cuts are alternated on the folding lines for the bottom and top flaps.

If required, cuts could be practiced on the bottom and top flaps, such that cells open on both sides.

According to another embodiment, not shown, lamellae are cut in the external sheet of the box panels. Such lamellae have a small width and extend through several cells.

The invention claimed is:

1. A box for sterile products comprising:
panels forming a belt (10) and
flaps extending the panels and forming bottom and top walls perpendicular to the belt,
wherein the belt and the flaps are cut in a foamed plastic material comprising at least two cover leaves (P1, P2), mutually spaced apart by means of a plurality of struts (E) providing mutually parallel longitudinal cells, characterized in that
at least the internal covering sheet is perforated (C) so as to allow for a sterilizing gas to pass through said covering sheet, the perforations allowing for gas to pass through, although preventing passage of dust,
and
cuts (13) go across at least the external covering sheet, being made along the hinging lines the top and bottom flaps (31 32 41 42 51 52 61 62) on the belt,
such that a part of cells A opens on cuts (13) at both ends thereof.

2. A box according to claim 1, wherein the cuts (13) thereof go across the external sheet (P2) alone.

3. A box according to claim 1, wherein the cuts (13) thereof along the hinging line of the bottom flaps alternate with the cuts (13) along the hinging line of articulation of the flaps in the top wall.

4. A box according to claim 2, wherein the cuts (13) thereof along the hinging line of the bottom flaps alternate with the cuts (13) along the hinging line of articulation of the flaps in the top wall.

* * * * *